United States Patent [19]

Sheets

[11] 4,328,595
[45] May 11, 1982

[54] INTRAOCULAR LENS

[76] Inventor: John H. Sheets, 2525 Palo Verde, Odessa, Tex. 79763

[21] Appl. No.: 71,375

[22] Filed: Aug. 30, 1979

[51] Int. Cl.³ .............................. A61F 1/16; A61F 1/24
[52] U.S. Cl. .......................................................... 3/13
[58] Field of Search ........................................ 3/13, 1

[56] References Cited

U.S. PATENT DOCUMENTS

| | | |
|---|---|---|
| 2,834,023 | 5/1958 | Lieb .................................. 3/13 X |
| 3,711,870 | 1/1973 | Deitrick ............................. 3/13 |
| 3,866,249 | 2/1975 | Flom ................................. 3/13 |
| 3,906,551 | 9/1975 | Otter ................................. 3/13 |
| 3,913,148 | 10/1975 | Potthast ............................. 3/13 |
| 3,922,728 | 12/1975 | Krasnov ............................. 3/13 |
| 3,925,825 | 12/1975 | Richards et al. .................... 3/13 |
| 3,986,214 | 10/1976 | Krasnov ............................. 3/13 |
| 3,991,426 | 2/1975 | Flom et al. ......................... 3/13 |
| 3,994,027 | 11/1976 | Jensen et al. ....................... 3/13 |
| 3,996,627 | 12/1976 | Deeq et al. ......................... 3/13 |
| 4,010,496 | 3/1977 | Neefe ................................. 3/13 |
| 4,014,049 | 3/1977 | Richards et al. .................... 3/13 |
| 4,025,965 | 5/1977 | Siegmund ........................... 3/13 |
| 4,028,082 | 6/1977 | Krohn et al. ....................... 3/13 |
| 4,041,552 | 8/1977 | Ganias .............................. 3/13 |
| 4,053,953 | 10/1977 | Flom et al. ......................... 3/13 |
| 4,056,855 | 11/1977 | Kelman ............................. 3/13 |
| 4,073,014 | 2/1978 | Poler ................................. 3/13 |
| 4,077,071 | 3/1978 | Freeman ............................ 3/13 |
| 4,079,470 | 3/1970 | Deeg et al. . |
| 4,085,467 | 4/1978 | Rainin et al. ...................... 3/13 |
| 4,110,848 | 9/1978 | Jensen .............................. 3/13 |
| 4,118,808 | 10/1978 | Poler ................................. 3/13 |
| 4,122,556 | 10/1978 | Poler ................................. 3/13 |
| 4,124,905 | 11/1978 | Clark ................................ 3/13 |
| 4,127,903 | 12/1978 | Schachar ............................ 3/13 |
| 4,134,160 | 1/1979 | Bayers .............................. 3/13 |
| 4,134,161 | 1/1979 | Bayers .............................. 3/13 |
| 4,139,915 | 2/1979 | Richards et al. .................... 3/13 |
| 4,143,427 | 3/1979 | Annis . |
| 4,149,279 | 4/1979 | Poler ................................. 3/13 |
| 4,159,546 | 7/1979 | Shearing ............................ 3/13 |
| 4,174,543 | 11/1979 | Kelman ............................. 3/13 |
| 4,873,015 | 2/1978 | Peyman et al. ..................... 3/13 |

FOREIGN PATENT DOCUMENTS

| | | |
|---|---|---|
| 959314 | 3/1957 | Fed. Rep. of Germany . |
| 2607462 | 12/1976 | Fed. Rep. of Germany . |
| 2717706 | 10/1978 | Fed. Rep. of Germany ............ 3/13 |
| 2239234 | 2/1975 | France . |
| 2313010 | 12/1976 | France . |
| 148232 | 7/1971 | Netherlands . |
| 810232 | 3/1959 | United Kingdom . |
| 563174 | 7/1977 | U.S.S.R. ................................ 3/13 |

OTHER PUBLICATIONS

Covered Bridge An Update on Lens Implantation by John H. Sheets, M.D. or Bridge over Troubled Waters (3rd Attempt) (Book) 1977, pp. 5–13.
Shepard, The Intraocular Lens Manual.
Nordlohne, The Intraocular Implant Lens Development and Results with Special Reference to the Binkhorst Lens (Book), The Williams & Wilkins Co., Baltimore, 1975.

*Primary Examiner*—Ronald L. Frinks
*Attorney, Agent, or Firm*—Mason, Fenwick & Lawrence

[57] ABSTRACT

An intraocular lens assembly for positioning in the posterior chamber of the eye has a plastic lens body supported in the eye by first and second flexible spring-like resilient support loops of circular cross-section extending symmetrically from opposite sides of the peripheral edge of the lens body; the outer end of each support loop is received in and biased against the equatorial region of the lens capsule of the eye from which the natural lens has been removed and has first and second outwardly protruding arcuate contact feet engaging the capsule and separated by an inwardly extending arcuate connector portion with first and second support legs extending from the opposite ends of the contact feet to chordal openings in the periphery of the lens body in which the inner ends of the support legs are fixedly embedded.

26 Claims, 4 Drawing Figures

INTRAOCULAR LENS

BACKGROUND OF THE INVENTION

This invention is in the field of intraocular lenses for correction of aphakia by implantation in the posterior chamber of the human eye. More specifically, the present invention is directed to an intraocular lens for self-centered non-sutured, positioning in the lens capsule of the human eye following extracapsular removal of the natural lens therefrom.

It has long been recognized and accepted that an intraocular lens implanted in the human eye following cataract surgery will provide substantially better vision than is possible with the use of either of the available alternatives of contact lens or spectacles. However, while the first intraocular lens implantations were begun by Dr. Harold Ridley in 1949, who implanted a plastic lens in the posterior chamber following an extracapsular cataract extraction, there were a large percentage of complications such as iritis, pupillary occlusion, dislocation of the lens and the like which prevented general acceptance of intraocular lens implantation.

A wide variety of lens constructions and surgical techniques subsequently evolved as the result of efforts to overcome the problems of the original Ridley lens. Generally speaking, the majority of subsequent efforts were directed toward the provision of a lens for implantation in the anterior chamber of the eye due primarily to the easier accessibility of the anterior chamber and the fact that the lens could be easily positioned by the surgeon in a manner not possible with a posterior chamber mounted lens. Earlier anterior chamber lenses were supported by contact with the anterior chamber angle and also frequently contacted the cornea. Entirely satisfactory results were not always achieved with the more frequent complications including corneal dystrophy resultant from endothelial contact, corneal edema, and inherent optical inadequacy in not providing full binocular vision and optical malfunction due to mispositioning. Subsequent anterior chamber positioning was achieved by fixation to the iris with the most successful lens of this general type being that of Binkhorst employing rigid posterior chamber loops extending through the pupil to the anterior chamber positioned lens. Unfortunately, erosion of the iris sometimes results with these and other iris contacting or attached lenses.

Other previously proposed lens attachment and mounting means have included rigid loops, arms, plates, legs and the like which have been held in place by sutures, such as exemplified by the rigid loops 12 and 13 in Jensen U.S. Pat. No. 4,110,848 and by rigid plates 12 and 13 of Kelman U.S. Pat. No. 4,092,743, with the sutures extending through the iris. Prongs 13 etc. extending through the iris are disclosed in the Flom U.S. Pat. No. 3,866,249. Jensen Pat. No. 3,994,027 and Peyman U.S. Pat. No. 4,073,015 both disclose rigid support loops engaging the anterior capsule wall.

Iris-engaging clip support for a posterior lens is shown in Richards et al U.S. Pat. No. 4,014,049. In many instances, the lens body itself also contacts the iris and in the case of the majority of posterior chamber implants, the lens body contacts or exerts pressure on the ciliary body in the manner of the original Ridley lens and as more recently exemplified in the aforementioned Richards et al patent and Potthast U.S. Pat. No. 3,913,148 so as to create the possibility of tissue necrosis.

Another recent posterior chamber lens is disclosed in Shearing U.S. Pat. No. 4,159,546 in which J-shaped elastic support members extend outwardly from opposite peripheral edges of the lens to engage the ciliary body, or possibly the lens capsule, to support the lens in position. Unfortunately, the J-shaped support members do not have substantial resistance to torsional twisting and flexing and it is consequently difficult to accurately and predictably position the lens and its support members in the posterior chamber.

For a more extensive treatment of prior known intraocular lenses, reference is also made to my prior publications Bridge Over Troubled Waters and Covered Bridge.

Notwithstanding the great strides made in lens implantation since the original Ridley activity as evidenced by the thousands of successful lens implantations, complications in individual cases continue to arise in a small percentage of the cases. In addition to the previously noted corneal and other problems, unsatisfactory results can arise from the lens becoming mispositioned for a variety of reasons such as erosion of the iris or the ciliary body portion of the eye with which the support and positioning elements are engaged. Improper sizing and excessive weight of the lens and support elements also causes subsequent mispositioning of the lens in some instances. It is consequently desirable to avoid the use of sutures and other similar connectors engaging viable portions of the eye and to minimize contact of the lens and its support means with the iris and ciliary body to the fullest extent possible.

SUMMARY OF THE INVENTION

Thus, it is the primary object of this invention to provide a new and improved intraocular lens.

A further object of this invention is the provision of a new and improved intraocular lens for posterior chamber implantation supported by the lens capsule.

Achievement of the foregoing objects is enabled by the preferred embodiment of the present invention which comprises a lens body having first and second spring-like flexibly deformable support loops of elastic wire-like shape extending outwardly in a symmetrical manner from opposite sides of the periphery of the lens body providing for the intraocular lens assembly an overall unstressed diameter greater than the diameter of the lens capsule causing the support loops to be biased against the equatorial region of the lens capsule in the area of the juncture of the anterior and posterior capsule walls. Each of the support loops is formed of a flexible unitary spring-like material such as polypropylene with each loop having its outer extent defined by first and second arcuately curved contact feet separated by an inwardly extending arcuate connector portion with the opposite sides of the contact feet being respectively unitarily connected to first and second leg components extending to the lens body. The first and second leg components diverge outwardly from the lens and are oriented so that the first contact foot will in most instances engage the equatorial region of the lens capsule with less force than will the second contact foot. The inner ends of the leg members are connected to the lens by conventional bonding techniques. The locations of the inner ends are such that the chords formed by an imaginary extension of the leg members are separated by approximately 27°. The arrangement is such that the lens is easily and automatically accurately positioned within the lens capsule of the eye vertically, horizontally and rotationally simply by the spring action of the support loops in contact with the interior surface of the lens capsule. There is normally no need to effect suturing of the support means to any portion of the eye and there is ordinarily an absence of contact with the ciliary body. Since the lens capsule is formed of firm, essentially non-viable tissue, inflammation, trauma and erosion are substantially less likely to occur than is the case with prior art devices supported by or contacting the ciliary body and/or the iris or using rigid plates or other types of loops contacting the capsule. Since each support loop provides two spaced contact foot areas of capsule contact, a total of four contact support areas serve to engage the capsule to provide a secure and reliable support for the lens body.

A better understanding of the manner in which the preferred embodiment achieves the objects of the invention will be enabled when the following detailed description is considered in conjunction with the appended drawings in which like reference numerals are employed in the different figures for identification of the same component parts of the preferred embodiment.

DESCRIPTION OF THE PREFERRED EMBODIMENT

Figure 1:
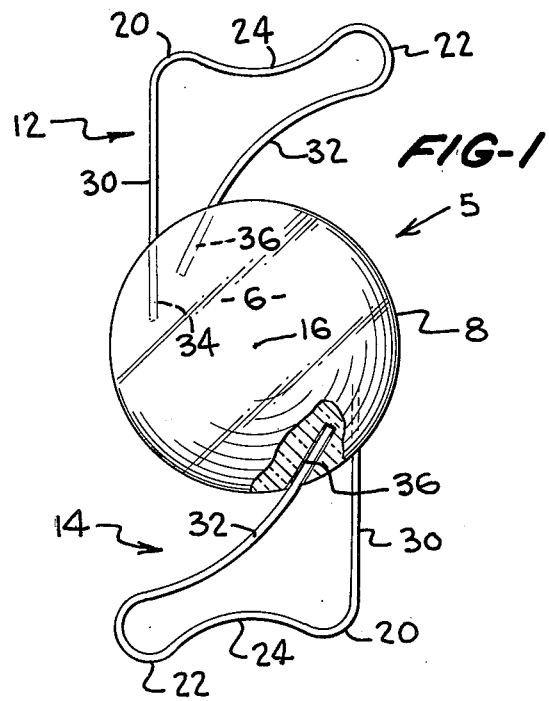
FIG. 1 is a front elevation view of the preferred embodiment of the invention.

The preferred embodiment 5 of the invention basically consists of a molded lens body 6 formed of optical plastic such as polymethylmethacrylate. The lens body 6 of 4 mm to 6 mm diameter is provided with a planar posterior face 7, a cylindrical peripheral surface 8 and a spherical anterior face 9 of desired curvature to give the required optical characteristics for the particular patient in which it is to be implanted. Support and retention of the lens body 6 is provided by a first spring-like support loop 12 and a second spring-like support loop 14 with the support loops being of elastic wire-like shape formed of circular cross-section polypropylene or other similar flexible material of approximately 0.15 mm diameter. Loops 12 and 14 are preferably positioned in a common plane perpendicular to and symmetrically with respect to the optical and geometric axis 16 of the lens body 6 with the outermost portions of the respective loops when in their relaxed condition of FIGS. 1 and 2 being approximately 12 mm apart. In some instances, it might be desirable to cant the loops with respect to the lens axis.

Figure 2:
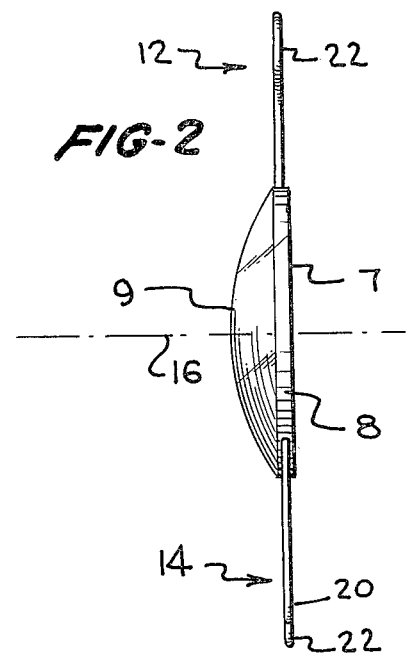
FIG. 2 is a side elevation view of the preferred embodiment.
Figure 3:
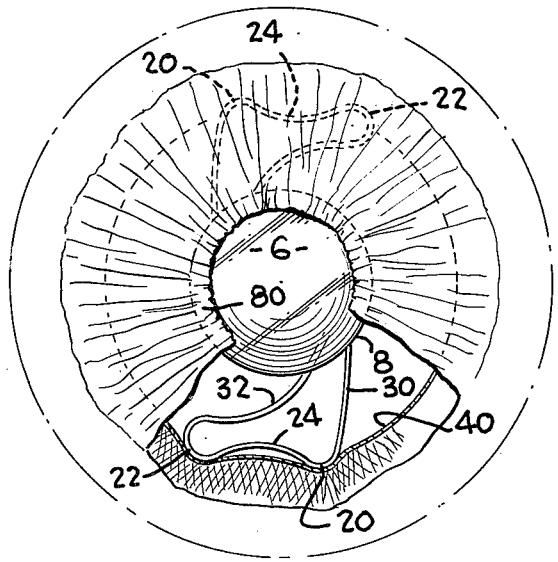
FIG. 3 is a front elevation view of the preferred embodiment as implanted in the eye with portions removed for clarity of illustration.

The first and second support loops are in the form of identical configuration with each including a first contact foot portion 20 and a second contact foot portion 22 with each foot portion being of arcuate axial configuration having a center of curvature between it and the lens body 6 as will be apparent from inspection of FIG. 1. The arcuate extent of the first contact foot 20 is less than 180° while the arcuate extent of the second contact foot 22 exceeds 180°. Contact foot portions 20 and 22 are connected by an inwardly extending oppositely curved arcuate connector portion 24 which has a center of curvature positioned outwardly from itself with respect to the lens body 6. The contact foot portions 20 and 22 of the two support loops 12, 14 in their relaxed condition are spaced apart a sufficient distance such that the overall diameter of the lens assembly is greater than the diameter of the lens capsule, causing the contact foot portions to resiliently engage and press outwardly the equatorial surface of the capsular membrane, as illustrated in FIG. 3, to retain the lens portion within the lens capsule and center it within the capsule. It should also be observed that the second contact foot portion 22 is positioned radially outwardly a greater distance from the lens body 6 than is the first contact foot portion 20 so that when the lens is positioned within the capsular membrane, second contact foot portion 22 engages the membrane with slightly greater force than does the first contact foot portion 20 when positioned in a normally sized lens capsule; however, in some instances where the capsule is smaller, the first contact foot 20 can engage the capsule with greater force than second contact foot 22. Inward movement of second contact foot 22 as a result of positioning of the loops 12 and 14 in the capsule as in FIG. 3 brings the curved connector portion 24 into closer proximity with the second support leg 32 than is the case when the loops are in their relaxed condition of FIG. 1.

Additionally, each of the support loops includes a first support leg 30 of linear configuration and a second support leg 32 of arcuate configuration. Support legs 30 and 32 diverge outwardly from the periphery 8 of the lens body 6 and are respectively connected to first and second end portions 34 and 36 of the loops chordally positioned inside the lens body and bonded thereto by a heat probe or ultrasonic probe in a conventional manner.

Figure 4:
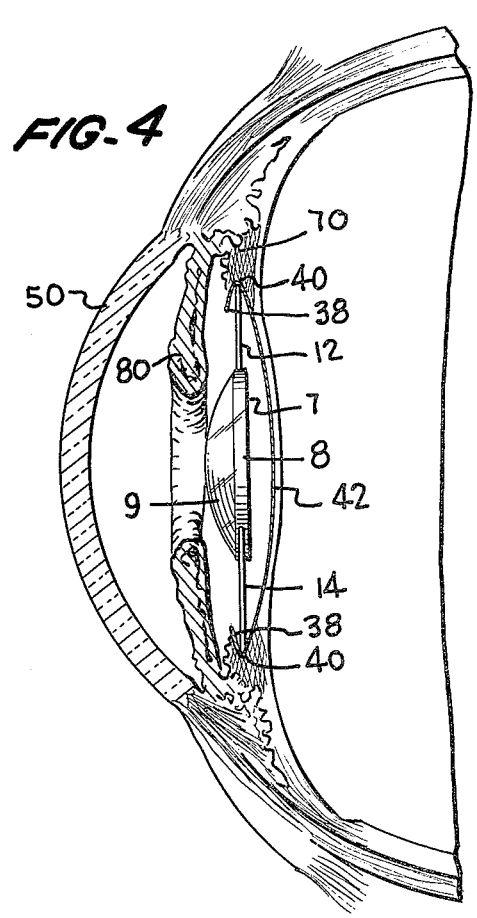
FIG. 4 is a bisecting sectional view of the eye of FIG. 3 with the lens in implanted position.

Preparation of the eye for receipt of the preferred embodiment is effected by a conventional extracapsular cataract removal procedure in which the central portion of the anterior wall 38 of the lens capsule is removed along with the natural lens so as to leave the equatorial region 40 and posterior wall 42 of the lens capsule in position as shown in FIG. 4.

Thus, when the preferred embodiment 5 is positioned in the eye as shown in the drawings, there is basically a four-point support for the lens which resists rotation and other lens movement with the resilient spring-like nature of the support loops serving to center the lens with respect to the optic axis of the eye in a position closely corresponding with the position of the original natural lens as shown in FIG. 3. There is some deflection of the equatorial region 40 of the lens capsule and the main contact therewith of each loop is at contact foot portions 20 and 22 with some medial contact along the connector portion 24 depending on the extent to which the lens capsule is deflected by the portions 20 and 22. Since foot portion 22 engages the lens capsule with greater force than foot portion 20, except in rare cases where the capsule is unusually small, the area of the lens capsule engaged by portion 22 is deflected radially outwardly a greater distance than the area engaged by foot portion 20. There is no contact with the iris or any other easily injured vascular eye component with all contact being between the support loops 12 and 14 and the relatively tough non-traumatic avascular tissue of the lens capsule. There is an absolute and complete lack of any need for sutures, clamps, prongs or the like for retaining the lens in position. By employing capsular fixation, there is little chance of pseudophacodenesis. The ciliary body 70 and iris 80 are not contacted with any substantial force by the lens or loops and the likelihood of damage to either is consequently avoided.

In addition to the foregoing, the present invention by using relatively small loops provides substantial advantages over the prior art in that it can be positioned in the eye through a relatively small inverted V-shaped incision in the anterior wall of the capsule. Since the support loops do not have to extend radially outwardly to the area of the ciliary body, they can consequently be substantially smaller than is the case with lens such as the Shearing lens in which support members are engaged with the ciliary body. In addition to enabling an easier positioning in the eye, the present invention is also consequently easier to remove in the event removal is required. Additionally, the present invention permits the use of a single plane lens so as to substantially reduce the chance of damage to the corneal endothelium. The flexible nature of the loops permits the use of a single size for all eyes to provide a distinct advantage over rigid loops, plates and the like previously employed for lens support. Connection of the support loops to the lens at both ends provides sufficient resistance to twisting deflection of the loops to ensure substantially easier and more accurate positioning in the eye than is possible with the J-shaped support system of Shearing.

It should also be noted that there is a good chance of the obtainment of satisfactory results even in circumstances in which the present invention is improperly positioned in the eye such as, for example, with one of the contact feet being out of the capsule.

Further, since there is no contact with the iris, complete dilation of the eye is possible and it is easy for the doctor to do subsequent ophthalmoscopy.

Numerous modifications of the preferred embodiment will undoubtedly occur to those of skill in the art, for example, the lens body and loops could be formed unitarily. It should be understood that the spirit and scope of the invention is not limited to the preferred embodiment but is to be limited solely by the appended claims.

I claim:

1. An intraocular lens assembly for self-centering positioning and support in the lens capsule of the eye solely by interaction of its hereinafter defined flexible wire-like support loops with confronting equatorial surfaces of the lens capsule comprising a lens body, first and second support members extending from the periphery of the lens body for engaging the lens capsule having an overall unstressed diameter greater than the diameter of the lens capsule, at least one of said support members comprising a spring-like flexibly deformable support loop of elastic wire-like shape extending outwardly from said lens body and including first and second end portions captured in the lens body at first and second attachment locations on the periphery of the lens body, said loop being shaped to provide a first contact foot portion extending a substantial distance outwardly beyond adjacent portions of the support loop and positioned to engage one area of the lens capsule with an outward radial force and a second contact foot portion spaced from the first contact foot portion extending a substantial distance outwardly beyond adjacent portions of the support loop and positioned to engage a second area of the lens capsule with an outward radial force wherein said first contact foot portion and said second contact foot portion are unsecured to viable body tissue when implanted in the lens capsule and dimensioned and shaped so that they provide substantially the only contact between the support loop and the lens capsule and exert radial and circumferential resilient forces urging the lens to centered position in the lens capsule.

2. The intraocular lens assembly of claim 1 wherein said support loop includes an inwardly extending connector portion positioned inwardly of and between the first contact foot portion and the second contact foot portion.

3. The lens assembly of claim 2 wherein said spring-like flexible support loop additionally includes a first support leg extending between said first end portion and said first contact foot portion and a second support leg extending between the second end portion and the second contact foot portion.

4. The lens assembly of claim 3 wherein the first and second end portions of said spring-like support loop extend inwardly from the peripheral edge of the lens body in linear chordal orientation with respect to the lens body.

5. The lens assembly of claim 2 wherein said support members further include a second spring-like flexible support loop which is identical to said first-mentioned support loop, said support loops being positioned on said lens body in symmetrical relation to each other with each support loop further including first and second outwardly diverging support legs respectively connected to said first contact foot portion and said second contact foot portion on their outer ends and to said first and second end portions their inner ends.

6. An intraocular lens assembly for self-centering positioning and support and retention in the lens capsule of the eye solely by interaction of its hereinafter defined flexible wire-like support loops with confronting equatorial surfaces of the lens capsule comprising a lens body, first and second spring-like flexibly deformable support loops of elastic wire-like shape extending outwardly from the periphery of said lens body for engaging the lens capsule having an overall unstressed diameter greater than the diameter of the lens capsule, each of said support loops including first and second end portions captured in the lens body at first and second attachment locations, each said loop being shaped to provide a first contact foot portion extending a substantial distance outwardly beyond adjacent portions of the support loop and positioned to engage one area of the lens capsule with an outward radial force and a second contact foot portion extending a substantial distance outwardly beyond adjacent portions of the support loop and spaced from the first contact foot and portioned to engage a second area of the lens capsule with an outward radial force wherein said first and second contact foot portions are unsecured to viable body tissue when implanted in the lens capsule and dimensioned and shaped so that they constitute substantially the only portions of each support loop engaging the lens capsule and exert radial and circumferential resilient forces urging the lens to centered position in the lens capsule.

7. The lens assembly of claim 6 wherein each of said support loops includes an inwardly extending connector portion positioned inwardly of and between the first contact foot portion and the second contact foot portion.

8. The lens assembly of claim 7 wherein each of said support loops further includes a first support leg extending between the first end portion and the first contact foot portion and a second support leg extending between the second end portion and the second contact foot portion.

9. The lens assembly of claim 8 where the first and second end portions of each support loop extend inwardly from the peripheral edge of the lens body in linear chordal orientation with respect to the lens body.

10. The lens assembly of claim 7 wherein said first and second support loops are positioned on said lens body in symmetrical relationship to each other with each support loop further including first and second outwardly diverging support legs respectively connected to said first contact foot portion and said second contact foot portion on their outer ends and to said first and second end portions on their inner ends.

11. The lens assembly of claim 10 wherein the first and second end portions of each support loop extend inwardly from the peripheral edge of the lens body in linear chordal orientation with respect to the lens body.

12. The lens assembly of claim 10 wherein said first contact foot portion and said second contact foot portion are of curved configuration each having a center of curvature positioned between each respective contact foot portion and said lens body.

13. The lens assembly of claim 10 wherein said first support leg is normally of linear configuration and said second support leg is normally of curved configuration and curves outwardly away from the first support leg.

14. The lens assembly of claim 6 wherein each of said support loops includes an inwardly extending connector portion positioned inwardly of and between the first contact foot portion and the second contact foot portion and said second contact foot portion is normally positioned when in a relaxed state a greater radial distance from the axis of the lens body than is said first contact foot portion.

15. The lens assembly of claim 14 wherein each of said support loops further includes a first support leg extending between the first end portion and the first contact foot portion and a second support leg extending between the second end portion and the second contact foot portion.

16. The lens assembly of claim 15 wherein the first and second end portions of each support loop extend inwardly from the peripheral edge of the lens body in linear chordal orientation with respect to the lens body.

17. The lens assembly of claim 16 wherein said first contact foot portion, said second contact foot portion and said connector portion are of curved configuration with each of said contact foot portions having a center of curvature positioned between each respective contact foot portion and said lens body.

18. The lens assembly of claim 17 wherein said first support leg is normally of linear configuration and said second support leg is normally of curved configuration and curves outwardly away from the first support leg.

19. The lens assembly of claim 6 wherein said support loops are positioned in a common plane extending perpendicular to the axis of said lens body.

20. The lens assembly of claim 19 wherein each of said support loops includes an inwardly extending connector portion positioned inwardly of and between the first contact foot portion and the second contact foot portion.

21. The lens assembly of claim 20 wherein each of said support loops further includes a first support leg extending between the first end portion and the first contact foot portion and a second support leg extending between the second end portion and the second contact foot portion.

22. The lens assembly of claim 21 wherein the first and second end portions of each support loop extend inwardly from the peripheral edge of the lens body in linear chordal orientation with respect to the lens body.

23. The lens assembly of claim 19 wherein each of said support loops includes an inwardly extending connector portion positioned inwardly of and between the first contact foot portion and the second contact foot portion and said second contact foot portion is normally positioned a greater radial distance from the axis of the lens body than is said first contact foot portion.

24. The lens assembly of claim 23 wherein each of said support loops further includes a first support leg extending between the first end portion and the first contact foot portion and a second support leg extending between the second end portion and the second contact foot portion.

25. The lens assembly of claim 24 wherein the first and second end portions of each support loop extend inwardly from the peripheral edge of the lens body in linear chordal orientation with respect to the lens body.

26. The lens assembly of claim 25 wherein said first contact foot portion, said second contact foot portion and said connector portion are of curved configuration with each of said contact foot portions having a center of curvature positioned between each respective contact foot portion and said lens body.

* * * * *